US009277979B2

United States Patent
Ikkink et al.

(10) Patent No.: US 9,277,979 B2
(45) Date of Patent: *Mar. 8, 2016

(54) DENTAL POSITION TRACKING SYSTEM FOR A TOOTHBRUSH

(71) Applicant: KONINKLIJKE PHILIPS N.V., Eindhoven (NL)

(72) Inventors: Teunis Jan Ikkink, Geldrop (NL); Hans Marc Bert Boeve, Hechtel-Eksel (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 75 days.

This patent is subject to a terminal disclaimer.

(21) Appl. No.: 14/199,284

(22) Filed: Mar. 6, 2014

(65) Prior Publication Data

US 2014/0246049 A1   Sep. 4, 2014

Related U.S. Application Data

(63) Continuation of application No. 12/866,381, filed as application No. PCT/IB2009/050695 on Feb. 19, 2009, now Pat. No. 8,690,579.

(60) Provisional application No. 61/061,056, filed on Jun. 12, 2008, provisional application No. 61/015,846, filed on Feb. 27, 2008.

(51) Int. Cl.
*A46B 15/00* (2006.01)
*A61C 17/22* (2006.01)

(52) U.S. Cl.
CPC ........... *A61C 17/221* (2013.01); *A46B 15/0002* (2013.01); *A46B 15/004* (2013.01); *A46B 15/0006* (2013.01); *A46B 15/0038* (2013.01); *A46B 2200/1066* (2013.01); *A61C 17/22* (2013.01)

(58) Field of Classification Search
CPC ........... A46B 15/0002; A46B 15/0006; A46B 15/0038; A46B 15/004; A46B 2200/1066; A61C 17/22; A61C 17/221
USPC ........................................................ 434/263
See application file for complete search history.

(56) References Cited

U.S. PATENT DOCUMENTS 6,731,213 B1   5/2004 Smith
2007/0270221 A1   11/2007 Park et al.

FOREIGN PATENT DOCUMENTS

WO   2007032015 A2   3/2007

*Primary Examiner* — Sam Yao
*Assistant Examiner* — Eddy Saint-Vil

(57) ABSTRACT

The dental position tracking system includes a toothbrush (30) which has a system (20) for determining the orientation of the toothbrush in the mouth of a user relative to the earth, based on measured stored information. Information is stored in the toothbrush concerning target ranges of expected measured toothbrush orientations for each of a plurality of dental zones (22). A processor (24) compares the measured toothbrush orientation information with the target orientation ranges, following conversion of both the target orientation information and the measured toothbrush orientation information to the same coordinate system. The processor then determines which if any of the target ranges matches, within a selected tolerance thereof, with the toothbrush orientation information. Any difference between the target range and the measured toothbrush orientation information is then used to partially adjust the target information range, in order to compensate for a change of position of the user's head.

20 Claims, 3 Drawing Sheets

DENTAL POSITION TRACKING SYSTEM FOR A TOOTHBRUSH

This invention relates generally to systems which track the position of a toothbrush in the mouth relative to a region or regions of teeth (dental zones) during brushing, and more specifically concerns such a system which takes into account movement of the head during brushing.

Real-time feedback as the user is brushing his/her teeth is a desired feature in a toothbrush. One important piece of information concerns the length of time that the toothbrush is used in different dental positions or zones, i.e. specific teeth regions covering a number of adjacent teeth. This information helps the user to determine the quality of brushing relative to each dental zone. Users can thus determine, for instance, whether they are underbrushing or overbrushing in terms of time for each dental zone.

One known technique for obtaining this information includes determining the orientation of the toothbrush as the user brushes his/her teeth and then correlating that orientation information with various pre-selected dental zones, since the orientation of the toothbrush will vary in a known manner depending upon the particular region or dental zone being brushed, e.g. a toothbrush will be oriented differently depending on whether the teeth being brushed are in the lower or upper jaw, and the particular surface being brushed is the outside, inside or chewing surface. A toothbrush having accelerometer and magnetometer sensors mounted thereon is capable of developing this orientation information. Such a system is disclosed in publication WO 2006/1378648A1. Accelerometers are used to measure gravity, while magnetometers measure the earth's magnetic fields. With this information, orientation information of a toothbrush relative to the earth (in an earth-based coordinate system) can be determined.

A significant problem with this approach per se, however, is that the user must keep his/her head still while brushing. The dental zone determinations are made based on the head being held in a particular known orientation. If the head orientation changes (the head moves/rotates) significantly during brushing in a given zone, the measured orientations will change accordingly for that zone, and these new measured orientations may no longer match with the fixed "target" toothbrush orientations for that dental region. The dental region thus may not be recognized or an incorrect dental region may be identified. Significant head movements are very common during a two-minute brushing interval. One solution is to measure head orientation changes by use of a reference sensor on the user's head which has a fixed orientation relative to the user's head. Changes in the target orientations can be made accordingly. However, using a separate sensor on the user's head is not convenient, adds additional expense and is unlikely to be consistently used.

Hence, it is desirable to have a dental position tracking system which includes obtaining toothbrush orientation information by use of accelerometers and magnetometers, but which also includes the ability to accurately take into account movement of the head during brushing without the need for a separate sensor.

Accordingly, a dental zone tracking system for a toothbrush which compensates for head movement during brushing is disclosed, comprising: a toothbrush which includes a system for determining the orientation of the toothbrush in the mouth of a user; stored target information for toothbrush orientation for each of a plurality of selected dental zones; a processing system for comparing the toothbrush orientation information with the target orientation information, once the toothbrush orientation information and the target orientation information are both in the same coordinate system and determining which, if any, target information matches, within a selected tolerance, the toothbrush orientation information; a compensation system which produces adjusted target information for the dental zones based on differences between the toothbrush orientation information and previous target information; and an information system responsive to the processing system for providing feedback information to the user concerning brushing in the selected dental zones.

Also disclosed is a method of dental zone tracking system for a toothbrush which compensates for head movement during brushing, comprising the steps of: determining the orientation of the toothbrush in the mouth of a user; storing target information for toothbrush orientation for each of a plurality of selected dental zones; comparing the toothbrush orientation information with the target orientation information, once the toothbrush orientation information and the target orientation information are both in the same coordinate system and determining which, if any, target information matches, within a selected tolerance, the toothbrush orientation information; adjusting target information for the dental zones based on differences between the toothbrush orientation information and previous target information; and providing feedback information to the user concerning brushing in the selected dental zones.

In the present system, toothbrush orientation information (in the mouth) is obtained in an earth-based coordinate system by accelerometer and magnetometer sensors in a manner similar to that described in the '648 publication or other conventional, well-known manner. This orientation information, referred to as measured toothbrush orientation information, is also used in the present system to determine changes of the position of the user's head (rotation), by tracking differences between the measured orientations and the pre-established fixed target orientations for the dental zones, such differences being caused by head movement. This enables the system to accurately identify dental regions in which the toothbrush is located even when the user is moving his/her head. Time of brushing information is then accurately obtained for each dental zone/region.

Figure 3:
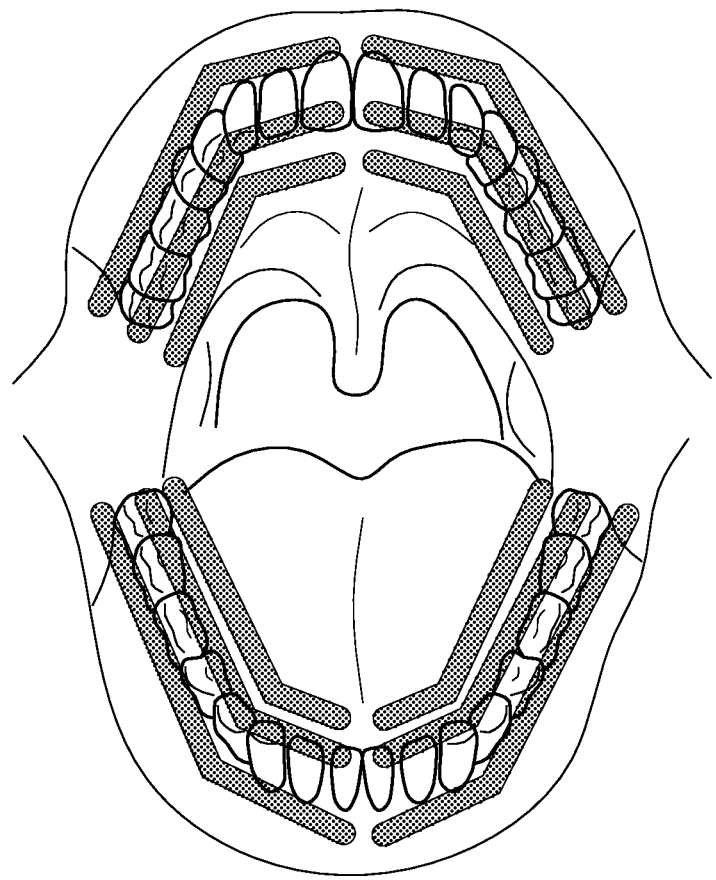
FIG. 3 is a view showing the dental zones in a user's mouth.

A system of dental zone position tracking first requires identifying the number of dental zones in the mouth, e.g. the zones may be divided according to the jaw (upper/lower), the surfaces of the teeth (outside surface, chewing surface, inside surface) and a particular jaw half (right/left). This is represented in FIG. 3. This particular arrangement thus divides the mouth into twelve different dental zones or regions, for example, one zone/region could cover the outside surfaces of the teeth in the left half of the lower jaw. Fewer or greater numbers of zones may be used. For a greater number of zones, the teeth at the front of the jaw may be distinguished from the teeth at the rear of the jaw.

A key consideration in dental position tracking is that each of the dental zones has a range of known valid toothbrush orientations associated with it, referred to as target orientations, given the head being in a particular position. These target ranges are defined in a head-based coordinate system, while the measured toothbrush orientations, determined from accelerometer and magnetometer sensor data, are relative to an earth-based coordinate system. Comparisons are made when the target orientations ranges and the measured orientations are expressed in the same coordinate system. If the measured toothbrush orientation is within one of the target ranges, it is concluded that the user is brushing his/her teeth in the dental zone having that target range. The time spent in each dental zone can then be tracked and that information provided to the user for confirmation or modification of brushing habits. Further, in a real-time situation, information can be provided as to how much time should still be used for each zone.

The target range of orientations for each dental position includes one dimension that is associated with the ideal orientations within the zone, as well as two orthogonal dimensions that indicate an allowable orientation tolerance relative to the ideal target orientation.

The target ranges for each dental zone are stored in memory in the toothbrush. As indicated above, the target orientation ranges are defined in a head-based coordinate system, while the measured toothbrush orientations which are determined from the accelerometer and magnetometer sensor data are represented in an earth-based coordinate system. Comparison of the two to determine dental zone requires that both be expressed in the same coordinate system. It is computationally less intensive to convert the target range of orientations to the earth-based coordinate system than vice versa, although, alternatively, the measured orientations could be converted to the head-based coordinate system for comparison.

In order to accommodate changes in head position during brushing, continuous transformation of the target range orientation information into an earth-based coordinate system is done. In the present system, this is accomplished in two steps, which account for changes in head position (rotation) during brushing, in order to accurately identify the dental zone being brushed. In a first step, the initial head position is established at the time the user starts the brushing session. The initial head position can be determined very accurately only if the initial toothbrush orientation in the head-based coordinate system is known. Knowing the initial toothbrush orientation in the head-based coordinate system, while measuring the toothbrush orientation in the earth-based coordinate system, permits the determination of initial head position. In practice, however, it is likely sufficient just to know the initial dental zone being brushed, and hence the corresponding orientation range in the head-based coordinate system, rather than the exact head orientation in the head-based coordinate system. The user thus must begin brushing in a pre-selected dental zone and the processing system must know this starting location. There results a correlation between the measured toothbrush orientations and the target range of orientation for a pre-selected dental zone at the start of the brushing event. Any errors due to initial head orientation can be accommodated (gradually corrected) by the second step in the head tracking process.

In the second step, the head orientation is effectively tracked as the user may change it (or not) in the course of a brushing session. The measured toothbrush orientations are used to track changes in head orientation. If the head orientation changes, the measured toothbrush orientations will deviate from the target orientation range (which does not change directly from a change in head orientation) that corresponds to the dental zone being brushed, because the measured toothbrush orientations will change to follow the actual position of the teeth as the head orientation changes. If the head position does not change, then the measured orientations will be within the stored target orientation range for the dental zone being brushed. Deviation from the target orientation range but within a threshold value relative to the range indicates that the head orientation estimation should be adjusted (resulting in a change in the target orientation range) so that the target orientation range, as expressed in the earth coordinate system, gets closer to the measured toothbrush orientations. The change in head orientation produces a difference between the target orientation range and the measured orientation, which difference in head orientation is actually tracked, i.e. accommodated. The adjustment to be applied to the target orientation range could be the same as that which would be needed to turn (match) the range of target orientations with the measured toothbrush orientation. However, the full corrective adjustment is typically not made because of the presence of noise in the measured orientations; i.e. one sampling interval should not be used to make a full correction. The correction is hence somewhat less than a full correction, which can be varied between 0 (no correction) and 1 (full correction).

In the processing, if any measured toothbrush orientations are outside of the range (including the difference tolerance/threshold) that corresponds to the likely dental position zone, then the head orientation information and the target orientation range is not updated, since the orientation information outside of the threshold would likely indicate that the toothbrush is being moved by the user from one dental zone to another.

Figure 1:
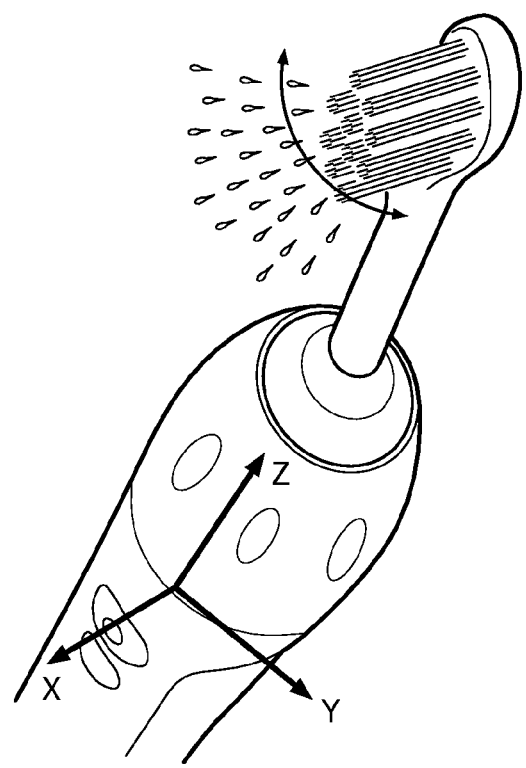
FIG. 1 is a perspective view of a toothbrush and a coordinate system relative to the toothbrush.
Figure 2:
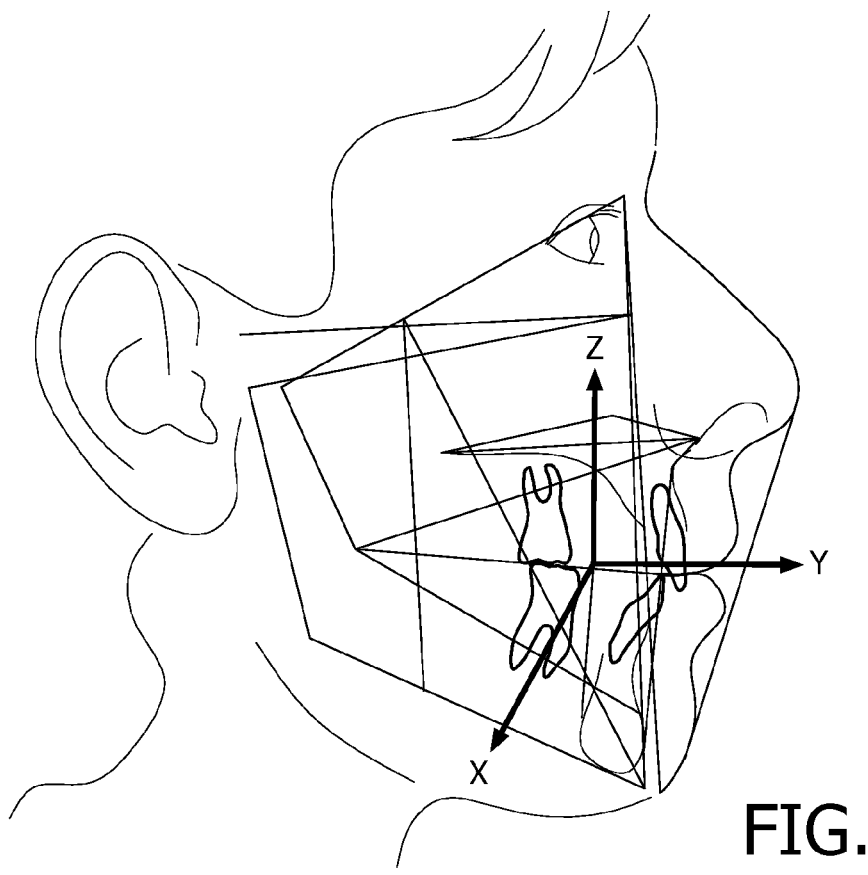
FIG. 2 is a side elevational view of a user's head and a coordinate system relative to the user's head.
Figure 4:
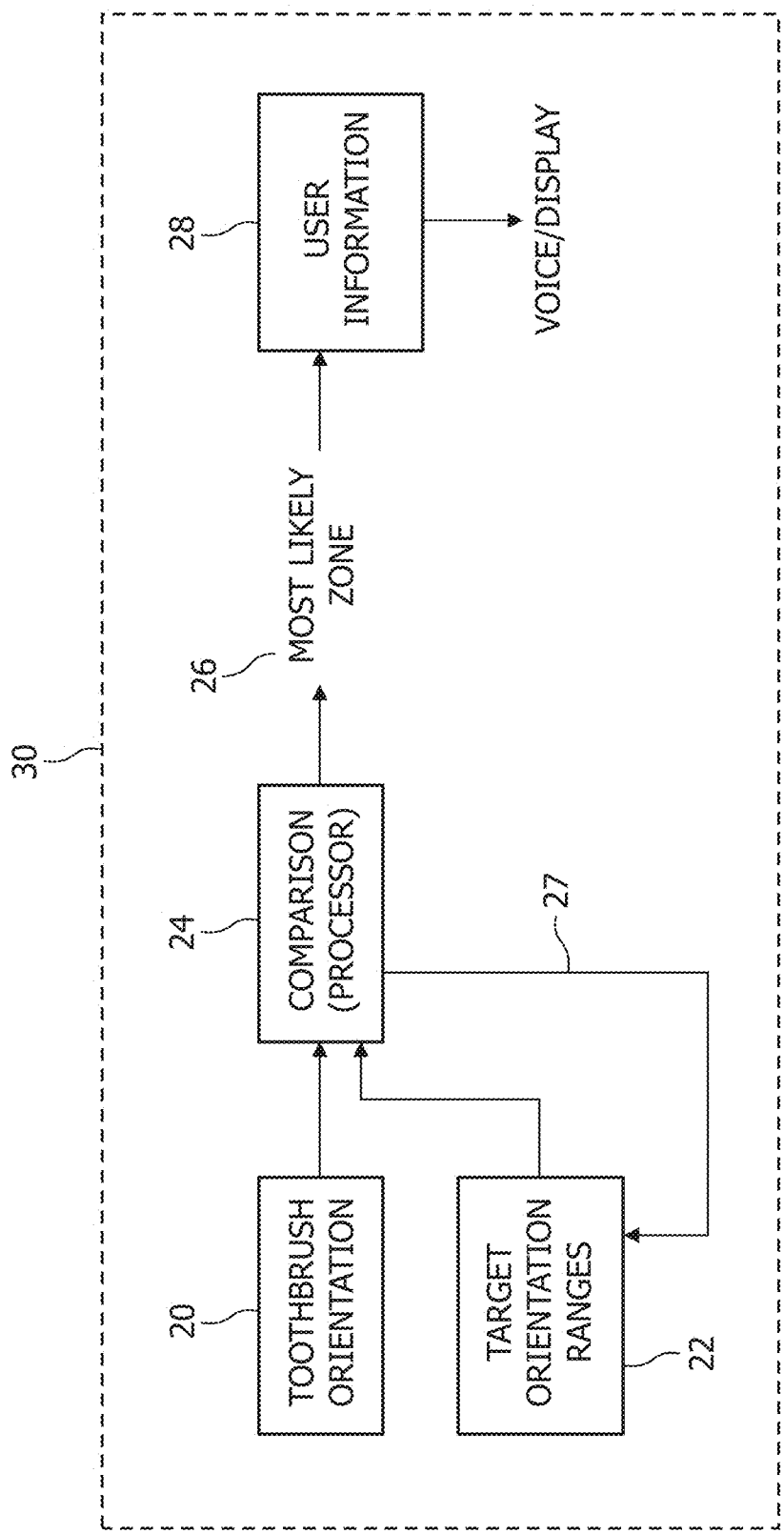
FIG. 4 is a system diagram representing the processing to accomplish dental zone tracking.

FIG. 1 shows the coordinate system for a toothbrush, while FIG. 2 shows a head-based coordinate system. In FIG. 1, the x-axis is in the direction of the bristles, the z-axis is along the shaft of the toothbrush and the y-axis is directed sideways (laterally) relative to the toothbrush. In FIG. 2, the z-axis is the direction from the bottom to the top of the head (perpendicular to the plane of the dental arch, the x-axis is the direction to the right of the head and the y-axis is the direction forward of the head. In the present system, orientation information of the toothbrush relative to the earth is determined from measured accelerometer and magnetometer information. This is shown at block 20 in FIG. 4. The calculation of the orientation information from gravity or the earth's magnetic field is briefly described below. The earth's gravity and magnetic field vectors have a fixed and known orientation in an earth-fixed reference coordinate system. They are identified below as $^r g$ and $^r B$ respectively, which are both three-dimensional vectors. Using a toothbrush having accelerometers and magnetometers mounted thereon, both vectors can be measured in the toothbrush-based coordinate system (FIG. 1) providing $^t g$ and $^t B$. The toothbrush orientation in the earth-fixed coordinate system can be expressed in a 3×3 matrix $^r T$. The columns of $^r T$ are the base vectors of the toothbrush-based coordinate system, expressed in the earth-based coordinate system. The relation between the representation of a vector V in the earth-based coordinate system $^r V$ and its representation in the toothbrush-based coordinate system $^t V$ is given by:

$$^r V = ^r T \cdot ^t V.$$

Thus, if the orthonormal set of 3D vectors is formed as follows:

$$\left( \text{east} = \frac{g \times B}{\|g \times B\|}, \text{north} = \frac{g \times B}{\|g \times B\|} \times \frac{g}{\|g\|}, \text{up} = \frac{-g}{\|g\|} \right)$$

the toothbrush orientation $^rT$ can be obtained as follows:

$$\left[\frac{^rg \times ^rB}{\|^rg \times ^rB\|} \quad \frac{^rg \times ^rB}{\|^rg \times ^rB\|} \times \frac{^rg}{\|^rg\|} \quad -\frac{^rg}{\|^rg\|}\right] =$$

$$^rT \cdot \left[\frac{^tg \times ^tB}{\|^tg \times ^tB\|} \quad \frac{^tg \times ^tB}{\|^tg \times ^tB\|} \times \frac{^tg}{\|^tg\|} \quad -\frac{^tg}{\|^tg\|}\right]$$

$$\Rightarrow {^rT} = \left[\frac{^rg \times ^rB}{\|^rg \times ^rB\|} \quad \frac{^rg \times ^rB}{\|^rg \times ^rB\|} \times \frac{^rg}{\|^rg\|} \quad -\frac{^rg}{\|^rg\|}\right] \cdot$$

$$\left[\frac{^tg \times ^tB}{\|^tg \times ^tB\|} \quad \frac{^tg \times ^tB}{\|^tg \times ^tB\|} \times \frac{^tg}{\|^tg\|} \quad -\frac{^tg}{\|^tg\|}\right]^T$$

the above set of vectors being arranged into a matrix. The superscript $^T$ indicates the matrix transpose operator and has been used to replace the matrix inverse operator, which is permitted since the operand matrix is unitary. The left hand-matrix factor (containing the vector representations in the earth-based coordinate system) can be precalculated. If east, north and up are adopted as the x, y, z base vector directions of the earth-based coordinate system, the left left-hand matrix becomes the identity matrix so that $$^rT = \left[\frac{^tg \times ^tB}{\|^tg \times ^tB\|} \quad \frac{^tg \times ^tB}{\|^tg \times ^tB\|} \times \frac{^tg}{\|^tg\|} \quad -\frac{^tg}{\|^tg\|}\right]^T$$

The above formula can be used to calculate toothbrush orientation from measured gravity and magnetic field vectors obtained from toothbrush-mounted accelerometer and magnetometer sensors. However, other techniques known in the art such as vector matching may be applied to improve accuracy of the orientation determination.

In the above determinations, the x-direction is more or less parallel to the bristle hairs (when the brush is not operating), so the result from the above calculations is orientation information for the toothbrush relative to the toothbrush coordinate system.

Each of the dental position zones is mapped onto a corresponding continuous range of toothbrush target orientations, which are time-fixed (invariant) when expressed in a head-based coordinate system, as shown in FIG. 2. This is represented at block 22 in FIG. 4. The beginning and end of each range (for a twelve-zone system) corresponds to brushing the incisors and the molars of a particular zone, i.e. the orientation range of the toothbrush from the incisors to the molars. As the brushhead is moved from the molars to the incisors in one dental zone, the toothbrush is typically rotated about a single axis. This axis is generally in the z-direction of the head-based coordinate system (perpendicular to the plane of the dental arch in FIG. 2). A complete zone definition (for twelve zones) in terms of toothbrush beginning and ending target orientation is shown in Table 1, identifying, for example, for each zone the selected tooth surfaces (outside, inside, chew) of the upper/lower jaw, either right or left side.

| Dental Position Zone | Rotation angle about toothbrush x-axis (in degrees) | | Toothbrush x-axis direction | |
|---|---|---|---|---|
| | begin | end | begin | end |
| Upper, Outside, Left | 80 | 80 | $(\sqrt{1-d^2}, -d, 0)$ | $(0, -1, 0)$ |
| Upper, Outside, Right | −80 | −80 | $(-\sqrt{1-d^2}, -d, 0)$ | $(0, -1, 0)$ |
| Upper, Chew, Left | 80 | 0 | $(0, 0, 1)$ | $(0, 0, 1)$ |
| Upper, Chew, Right | 100 | 180 | $(0, 0, 1)$ | $(0, 0, 1)$ |
| Upper, Inside, Left | −80 | −80 | $(-\sqrt{1-d^2}, d, 0)$ | $(0, 1, 0)$ |
| Upper, Inside, Right | 80 | 80 | $(\sqrt{1-d^2}, d, 0)$ | $(0, 1, 0)$ |
| Lower, Outside, Left | 100 | 100 | $(\sqrt{1-d^2}, -d, 0)$ | $(0, -1, 0)$ |
| Lower, Outside, Right | −100 | −100 | $(-\sqrt{1-d^2}, -d, 0)$ | $(0, -1, 0)$ |
| Lower, Chew, Left | 100 | 180 | $(0, 0, -1)$ | $0, 0, -1)$ |
| Lower, Chew, Right | 80 | 0 | $(0, 0, -1)$ | $(0, 0, -1)$ |
| Lower, Inside, Left | −100 | −100 | $(-\sqrt{1-d^2}, d, 0)$ | $(0, 1, 0)$ |
| Lower, Inside, Right | 100 | 100 | $(\sqrt{1-d^2}, d, 0)$ | $(0, 1, 0)$ |

The target orientations are represented with respect to the head-based coordinate system and is characterized by a rotation angle about the toothbrush x-axis and the direction of the toothbrush x-axis. When the toothbrush-based coordinate system is aligned to the head-based coordinate system, the rotation angle is zero and the toothbrush x-axis direction is (1,0,0). To brush the outside surfaces of the rear molars on the right half of the upper jaw, the toothbrush is rotated approximately +80° about the bristle hair direction and the bristle hairs are oriented in the $(\sqrt{1-d^2}, -d, 0)$ direction where d=cos (80°).

The target orientation ranges each have a beginning and an end. From the beginning orientation, the end orientation is reached by continued rotation of the toothbrush about a single rotation axis. In the specific example above, the unique rotation axis is parallel to the z-axis in the head-based coordinate system. In the example above, the beginning and ending orientations of each zone are spaced apart by an 80° rotation of the toothbrush.

The measured toothbrush orientation information is then compared at regular intervals (every so many milliseconds) to the target orientation ranges by a processor (block 24) in the toothbrush or a separate unit. Determination of the dental zone that is being brushed involves comparison of the measured toothbrush orientations (block 20) with the twelve possible target ranges (block 22). The most likely dental zone being brushed is the zone in which a target orientation range is closest to the measured orientation. If the closest target range differs too much from the measured orientation, i.e. outside of the threshold difference relative to the range, the brush is likely to not be in any of the dental position zones.

The difference between the target orientation range and the measured orientation is measured by the smallest rotation angle that is needed to get from one orientation to another. In this respect, the calculations are easier if orientations are expressed using quaternions. The calculation of the rotation angle between the measured orientation and the target range orientation represented by quaternions involves taking a dot-product of the two quaternions. The dot-product is proportional to the cosine of the rotation angle. Taking the inverse cosine of the dot-product gives the desired rotation angle that measures the orientation difference. If the magnitude of the rotation angle is smaller than the threshold or tolerance value (within the threshold) relative to a target range, the toothbrush is still likely to be within the dental zone corresponding to that target orientation range. Reasonable orientation threshold levels are in the range between 5°-20°.

As indicated above, target orientation ranges are characterized by beginning and ending toothbrush orientations. The intermediate target orientation quaternions are obtained by interpolation between the beginning and the end orientations. The set of target quaternions forms a circular arc in four-dimensional quaternion space. To find the distance between a measured orientation quaternion and a target orientation quaternion range, the first step is to find the single interpolated target quaternion along the arc which is closest to the measured quaternion. This is referred to as the optimal target quaternion. Once that target quaternion is identified, one may readily calculate its distance to the measured quaternion. This distance is the distance between the measured orientation quaternion and the target orientation quaternion range.

The target orientation ranges are converted from the head-based coordinate system to the earth-based coordinate system so that they can be compared to the toothbrush orientations which are determined in the earth-based coordinate system. This conversion is done by multiplying the quaternion representing head orientation with that representing the respective beginning or end of a target orientation range. However, as indicated above, in an alternative embodiment the measured toothbrush orientations are converted to the head-based coordinate system so they can be compared with the target orientation ranges already defined in that coordinate system. This conversion is done by multiplying the conjugate of the quaternion representing head orientation with the quaternion representing the measured toothbrush orientation.

As the user's head moves during the brushing session, the head orientation quaternion will typically need updating, resulting in adjustment in the target range. The change in head orientation is estimated on the assumption that if the measured orientation quaternions are found to deviate systematically from the target range associated with the identified dental position zone, this must be due to a change in head position. The head orientation, as indicated above, is then slowly adapted by successive adjustments in the target orientations such that the deviation (difference) within the threshold between the measured toothbrush orientation and the target orientations ultimately goes to zero. These adjustments are represented by the feedback line 27 between the processor block 24 and the target ranges block 22.

Generally, the error (difference) quaternion as determined produces a change in the target quaternion to match the measured toothbrush orientation quaternion. If the error quaternion is applied to change the head orientation quaternion, then the optimal target orientation quaternion would appear to coincide with the measured orientation quaternion. Generally, however, to avoid incorrect head orientation estimates and corresponding incorrect target orientation quaternions, due to noise in the measured quaternion, which would lead to poor dental zone identification, the head orientation estimation is updated on the basis of the expected head position change during brushing, which is typically relatively small. The full error quaternion is not applied, but rather a scaled-down version thereof. An example of the sequence of processing system steps using quaternions which includes updating of the head position information is as follows.

Use of the superscript $^r$ below indicates that the corresponding quantity (vector, matrix or quaternion) is expressed in the earth-based (reference) coordinate system. Likewise, superscript $^t$ indicates an expression in the toothbrush-based coordinate system, and superscript $^h$ indicates an expression in the head-fixed coordinate system.

(1) Determine toothbrush orientation matrix $^rT$ of current time step (interval) from measurements of gravity ($^tg$) and earth-magnetic ($B$) field vectors by toothbrush-based sensors (accelerometer & magnetometer).

$$^rT = \left[ \frac{^tg \times {}^tB}{\|{}^tg \times {}^tB\|} \quad \frac{^tg \times {}^tB}{\|{}^tg \times {}^tB\|} \times \frac{^tg}{\|{}^tg\|} \quad -\frac{^tg}{\|{}^tg\|} \right]^T$$

(2) Convert orientation matrix $^rT$ to quaternion $^rt$ of current time step by standard matrix-quaternion conversion process.

(3) Apply head quaternion $r^h$(pre) of previous time step to obtain toothbrush orientation in head-based coordinate system (i.e. $^ht$)

$$^ht = {}^rh^*(\text{pre}) \otimes {}^rt$$

where * denotes the quaternion conjugation operator and ⊗ denotes the quaternion product operator.

(4) Calculate a zone-optimal target quaternion $^hzo_i$ for each of the target orientation ranges [$^hZB_i$, $^hZE_i$] (i=0 ... 11) belonging to a dental position zone. The quaternion $^hZB_i$, is the beginning of the range whereas $^hZE_i$ is the end of the range. For each zone and its associated target orientation range, the zone-optimal target quaternion is the quaternion within the target range that has minimum distance to $^tt$.

(5) Calculate the distance between $^ht$ and each of the zone-optimal target quaternions $^hzo_i$ (i=0 ... 11). Also calculate the corresponding difference quaternion $^hdf_i = {}^ht \otimes {}^hzo_i^*$.

(6) Use the distances calculated in the previous step to identify the dental position zone of the current time step as the zone j whose corresponding zone-optimal target quaternion $^hZO_j$ is closest to $^ht$. The corresponding difference quaternion $^hdf_j$ is the instantaneous head orientation error quaternion $^hhe = {}^hdf_j$. If the smallest distance is larger than a predefined threshold relative to the range, no dental position is identified (the brush is between zones) and the instantaneous head orientation error quaternion is taken as (1,0,0,0).

(7) Transform the instantaneous head orientation error quaternion towards the earth-based coordinate system, $^rhe = {}^rh \otimes {}^hhe \otimes h^*$.

(8) Calculate a head update quaternion as a reduced version of the instantaneous head orientation error quaternion. Reduced version here means that the amount of rotation (i.e. the rotation angle) is reduced. It can be done by multiplying the 3D vector component (i.e. the last three scalar components) of the quaternion by a factor k (0<k≤1), followed by renormalization of the quaternion to unity. As an equation:

$$^rhu = \frac{(^rhe_0, k \cdot {}^rhe_1, k \cdot {}^rhe_2, k \cdot {}^rhe_3)}{\|(^rhe_0, k \cdot {}^rhe_1, k \cdot {}^rhe_2, k \cdot {}^rhe_3)\|}.$$

The factor k determines the response time of the head tracking algorithm; k=1 indicates instantaneous response, whereas k=0 indicates infinite long response. The optimal value of k is a compromise between rapid response (high k) and low noise (low k) of the head orientation estimate.

(9) Calculate the head quaternion of the current time step ′h(cur) by premultiplying the head quaternion of the previous time step ′h(pre) by the head update quaternion, ′he (cur)=′hu⊗ ′he(pre).

(10) Return to (1) for the next time step.

With respect to further information on the use of quaternions in general in the present system, a target orientation range is defined by a start quaternion $^hZB$, and an end quaternion $^hZE$. The entire range is the arc (circular segment) on the unit hypersphere that connects these two quaternions. The rotation needed to go from the orientation $^hZB$ towards the orientation $^hZE$ is given by the Span quaternion:

$$^hSpan = {^hZE} \otimes {^hZB^*}$$

This Span quaternion can be represented in the standard form:

$$^hSpan = \begin{bmatrix} \cos\frac{1}{2}\phi_{span} \\ {^hn}\sin\frac{1}{2}\phi_{span} \end{bmatrix}$$

where $\phi_{span}$ is the angle of rotation (to rotate from the begin (start) orientation towards the end orientation) and $^hn$ is the corresponding rotation axis (a 3D vector of unity length). The zone-optimal quaternion $^hzo$, is somewhere on the arc subtended by $^hZB$ and $^hZE$. Hence it can be expressed as:

$$^hzo = \begin{bmatrix} \cos\frac{1}{2}\phi_{opt} \\ {^hn}\sin\frac{1}{2}\phi_{opt} \end{bmatrix} \otimes {^hZB}$$

where $0 \leq \phi_{opt} \leq \phi_{span}$. The rotation angle $\phi_{opt}$ defines where on the arc the zone-optimal quaternion lies. If $\phi_{opt}=0$, the zone-optimal quaternion coincides with the start orientation $^hZB$, whereas, if $\phi_{opt}=\phi_{span}$, it coincides with the end orientation $^hZE$.

To find the correct $\phi_{opt}$, the arc is temporarily extended towards a full circle and calculate where on the circle the $\phi_{opt}$ would lie. Thereafter, $\phi_{opt}$ is truncated on the interval $0 \leq \phi_{opt} \leq \phi_{span}$. The position on the circle can be calculated from the equation:

$$\phi_{opt} = 2\arctan\frac{-{^hn} \cdot (-{^hZB_0}{^ht} + {^ht_0}{^hZB} - {^hZB} \times {^ht})}{{^hZB_0}{^ht_0} + {^hZB} \cdot {^ht}}$$

where $^hZB_0$ is the scalar (first) component of the $^hZB$ quaternion and $^hZB$ is the 3D vector part (last three components) of the $^hZB$ quaternion. Likewise $^ht_0$ is the scalar component of the $^ht$ (toothbrush) quaternion and $^ht$ is the 3D vector part of the $^ht$ quaternion. This position on the circle indicated by $\phi_{opt}$ has extremum distance (either minimum or maximum) from the toothbrush quaternion $^ht$. In principle there is always one position of minimum distance and one position of maximum distance. These positions are diametrically spaced on both the circle and the unit hypersphere (since the centres of circle and hypersphere coincide). In other words, both extrema are spaced $2\pi$ apart in terms of $\phi_{opt}$. Hence, these positions (of minimum and maximum distance) correspond to the same orientation and there is no need to determine the nature of the extremum indicated by the calculated $\phi_{opt}$.

The zone-optimal quaternion $^hzo$ finally becomes:

$$^hzo = \begin{cases} {^hZB}, & \phi_{opt} \bmod 2\pi \leq 0 \\ \dfrac{\begin{bmatrix} {^hZB_0}{^ht_0} + {^hZB} \cdot {^ht} - \\ {^hn}({^hn} \cdot (-{^hZB_0}{^ht} + {^ht_0}{^hZB} - {^hZB} \times {^ht})) \end{bmatrix} \otimes {^hZB}}{\sqrt{({^hn} \cdot (-{^hZB_0}{^ht} + {^ht_0}{^hZB} - {^hZB} \times {^ht}))^2 + ({^hZB_0}{^ht_0} + {^hZB} \cdot {^ht})^2}}, & 0 < \phi_{opt} \bmod 2\pi < \phi_{span} \\ {^hZE}, & \phi_{opt} \bmod 2\pi \geq \phi_{span} \end{cases}$$

This includes the truncation to $^hZB$ and $^hZE$. The mod (modulo) operator is included to treat both extremes in the same way. Normalization is necessary to ensure that the quaternion $^hzo$ has unity length.

Determination at regular time intervals of the dental zone where the toothbrush is brushing in accordance with the above takes into account possible change in head orientation of the user during brushing. This is accomplished by the processor 24 in the manner described in detail above using quaternions. Information is then developed for the user with respect to the amount of brushing time spent in each dental zone, based on toothbrush orientation, as indicated at block 28. This feedback information may be generated within the toothbrush itself, which is indicated by dotted lines 30 in FIG. 4, such as a voice, or by a separate device which could include voice and a display. The communication between the toothbrush and the separate device could be wireless or by a wire tether. The separate device could be a toothbrush-dedicated device, or it could be the user's PDA or mobile phone, equipped with a suitable wireless interface.

Real-time feedback is thus provided on the time spent in each dental position zone. Further, insufficiently brushed zones could be identified, as well as brushing efficiency, such as the fraction of the total brushing time spent in each zone. A variety of reports and information can be provided to the user, in real time. User feedback can also be provided in the form of brushing reports and brushing trends. The trends require a memory and a suitable user interface. The memory could take the form of a memory element which can be plugged into the separate device, or memory inside the user's PDA or mobile phone. The information could also be stored in the user's personal computer.

Hence, a system has been described for accurately tracking dental zones during brushing, by determining toothbrush orientation through the use of accelerometers and magnetometers, while also taking into account changes in the position of the user's head, by selected processing of the orientation information. Accurate information of the dental zones being brushed can be obtained, even if the user moves his/her head during brushing, without the need for a separate sensor on the user's head. This information can be processed to produce important feedback for the user concerning time spent in the various dental zones, and other related information.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A dental zone tracking system for a toothbrush which compensates for head movement during brushing, comprising:
   a toothbrush which includes a system (20) for determining the orientation of the toothbrush during brushing by a user;
   stored target information (22) for toothbrush orientation for each of a plurality of selected dental zones;
   a processing system (24) for comparing the toothbrush orientation information with the target orientation information, once the toothbrush orientation information and the target orientation information are both in the same coordinate system and for determining which, if any, target information matches, within a selected tolerance, the toothbrush orientation information;
   a compensation system (24) which produces adjusted target information for the dental zones based on differences between the toothbrush orientation information and previous target information, wherein the compensation system includes using a pre-selected initial dental zone being brushed to determine an initial head orientation information and wherein the head orientation information is updated by determining the difference between the toothbrush orientation information and the target range orientation information at time intervals; and
   a feedback system (28) responsive to the processing system for communicating brushing information to the user concerning brushing in the selected dental zones.

2. The system of claim 1, wherein the target information is in the form of a range of target orientations for each selected dental zone.

3. The system of claim 2, wherein the adjustment to the target information is less than the full difference between the toothbrush orientation information and previous target information.

4. The system of claim 2, wherein intermediate orientations within the range of target orientations are obtained by turning about a single rotation axis.

5. The system of claim 1, wherein the information system provides information to the user concerning the time spent brushing in each selected dental zone.

6. The system of claim 1, wherein the user feedback information is provided from the toothbrush.

7. The system of claim 1, wherein the user feedback information is in the form of audible communication.

8. The system of claim 1, wherein the user feedback information is provided by a device separate from the toothbrush.

9. The system of claim 8, wherein the separate device is a toothbrush-dedicated device, a PDA or a mobile phone.

10. The system of claim 1, wherein the user feedback information is in the form of audible information or a visual display.

11. The system of claim 1, wherein the plurality of dental zones includes the following teeth divisions: (1) of the outside teeth surfaces, the teeth chewing surfaces, the inside teeth surface; (2) one of the upper jaw, the lower jaw; and (3) one of the right jaw half and the left jaw half.

12. The system of claim 1, wherein the difference between the toothbrush orientation information and the target orientation information is determined by the angle of the shortest rotation to turn between the toothbrush orientation information and the target orientation information.

13. The system of claim 1, wherein the toothbrush orientation information is determined using measurements obtained by an accelerometer and a magnetometer, located on the toothbrush.

14. A method of dental zone tracking for a toothbrush which compensates for head movement during brushing of teeth by the toothbrush, comprising the steps of:
   determining an initial head orientation information using a pre-selected initial dental zone being brushed;
   determining (20) the orientation of the toothbrush within a user's mouth during brushing by a user;
   storing target information (22) for toothbrush orientation for each of a plurality of selected dental zones;
   comparing (24) the toothbrush orientation information with the target orientation information, once the toothbrush orientation information and the target orientation information are both in the same coordinate system and determining which, if any, target information matches, within a selected tolerance, the toothbrush orientation information, including using the determined initial head orientation information and updating the head orientation information by determining the difference between the toothbrush orientation information and the target range information at time intervals;
   adjusting (24) target information for the dental zones based on differences between the toothbrush orientation information and previous target information; and
   providing feedback (28) information to the user concerning brushing in the selected dental zones.

15. The method of claim 14, wherein the target information is in the form of a range of target orientations for each dental zone.

16. The method of claim 15, wherein the adjustment to the target orientation information is less than the full difference between the toothbrush orientation information and previous target information.

17. The method of claim 15, wherein the feedback information includes information concerning the time spent brushing in each dental zone.

18. The method of claim 14, wherein the user feedback information is provided from the toothbrush.

19. The method of claim 14, wherein the user feedback information is provided by a device separate from the toothbrush.

20. The method of claim 14, wherein the toothbrush orientation information is determined using measurements obtained by an accelerometer and a magnetometer, located on the toothbrush.

* * * * *